(12) United States Patent
Brown et al.

(10) Patent No.: US 7,488,345 B2
(45) Date of Patent: Feb. 10, 2009

(54) ENDOVASCULAR GRAFT WITH PRESSOR AND ATTACHMENT METHODS

(75) Inventors: Peter S. Brown, Palo Alto, CA (US);
Marcelyn A. Berlo, San Francisco, CA (US); Tina A. Ton, San Jose, CA (US);
Kim-Lien Dang, San Jose, CA (US);
Veronica Creech, Newark, CA (US);
Joanne L. Parker, Fremont, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 688 days.

(21) Appl. No.: 10/760,129

(22) Filed: Jan. 16, 2004

(65) Prior Publication Data

US 2005/0107866 A1    May 19, 2005

Related U.S. Application Data

(63) Continuation-in-part of application No. 10/165,763, filed on Jun. 7, 2002, now Pat. No. 7,261,733.

(51) Int. Cl.
*A61F 2/06*    (2006.01)
(52) U.S. Cl. ..................... 623/1.23; 623/1.34
(58) Field of Classification Search ....... 623/1.11–1.21, 623/1.23, 1.34; 606/191–198; 600/505, 600/587
See application file for complete search history.

(56) References Cited

U.S. PATENT DOCUMENTS

| | | | |
|---|---|---|---|
| 3,240,207 A | 3/1966 | Barker et al. | |
| 4,815,472 A | 3/1989 | Wise et al. | |
| 4,834,101 A | 5/1989 | Collison et al. | |
| 4,846,191 A | 7/1989 | Brockway et al. | |
| 4,881,410 A | 11/1989 | Wise et al. | |
| 4,953,387 A | 9/1990 | Johnson | |
| 5,013,396 A | 5/1991 | Wise et al. | |

(Continued)

FOREIGN PATENT DOCUMENTS

EP    0 646 365 A1    4/1995

(Continued)

*Primary Examiner*—Corrine McDermott
*Assistant Examiner*—Cheryl Miller
(74) *Attorney, Agent, or Firm*—RatnerPrestia

(57) ABSTRACT

A endovascular graft having sensing devices attached thereto to facilitate measurement of pertinent parameters within the vasculature into which the graft is implanted. Power sources and transmitters may be attached to the graft to facilitate transmission of measurements to a receiving device outside the patient's body. The sensing devices, may be electrically passive or integrated devices with measurement and transmission capability. The sensing devices may be attached to specific locations on the graft material or attached to the lumen, thereby providing pertinent parameters from critical points inside the vasculature, or may be dispersed over the surface of the graft material or within the lumen to provide a profile of pertinent parameters. The sensing devices may be attached to the graft material with one or two sutures using a running stitch to minimize graft bulk and may be coated with a material to inhibit or control tissue growth. Methods and apparatus for handling and protecting sensing devices can be employed where the sensing device is particularly fragile. Approaches for effectively and efficiently attaching sensing and other devices to medical devices can also be utilized and are described.

11 Claims, 12 Drawing Sheets

U.S. PATENT DOCUMENTS

| | | |
|---|---|---|
| 5,055,838 A | 10/1991 | Wise et al. |
| 5,059,543 A | 10/1991 | Wise et al. |
| 5,100,479 A | 3/1992 | Wise et al. |
| 5,113,868 A | 5/1992 | Wise et al. |
| 5,207,103 A | 5/1993 | Wise et al. |
| 5,377,524 A | 1/1995 | Wise et al. |
| 5,411,551 A | 5/1995 | Winston et al. |
| 5,427,975 A | 6/1995 | Sparks et al. |
| 5,531,121 A | 7/1996 | Sparks et al. |
| 5,547,093 A | 8/1996 | Sparks |
| 5,567,989 A | 10/1996 | Sim |
| 5,598,847 A | 2/1997 | Renger |
| 5,663,508 A | 9/1997 | Sparks |
| 5,676,696 A | 10/1997 | Marcade |
| 5,719,069 A | 2/1998 | Sparks |
| 5,749,920 A * | 5/1998 | Quiachon et al. .......... 623/1.23 |
| 5,756,900 A | 5/1998 | Arie et al. |
| 5,807,258 A | 9/1998 | Cimochowski |
| 5,915,281 A | 6/1999 | Sparks |
| 5,932,809 A | 8/1999 | Sparks et al. |
| 5,936,164 A | 8/1999 | Sparks et al. |
| 5,967,986 A | 10/1999 | Cimochowski |
| 6,015,387 A | 1/2000 | Schwartz et al. |
| 6,053,873 A | 4/2000 | Govari et al. |
| 6,109,113 A | 8/2000 | Chavan et al. |
| 6,159,156 A | 12/2000 | Van Bockel |
| 6,170,488 B1 | 1/2001 | Spillman, Jr. et al. |
| 6,171,253 B1 | 1/2001 | Bullister et al. |
| 6,206,835 B1 | 3/2001 | Spillman, Jr. et al. |
| 6,231,516 B1 | 5/2001 | Keilman et al. |
| 6,416,474 B1 * | 7/2002 | Penner et al. ............... 600/309 |
| 6,442,413 B1 | 8/2002 | Silver |
| 6,475,170 B1 * | 11/2002 | Doron et al. ................ 600/587 |
| 6,477,426 B1 | 11/2002 | Fenn et al. |
| 6,610,096 B2 | 8/2003 | MacDonald |
| 6,840,956 B1 * | 1/2005 | Wolinsky et al. ........... 623/1.13 |
| 2002/0045921 A1 | 4/2002 | Wolinsky et al. |
| 2002/0183628 A1 * | 12/2002 | Reich et al. ................. 600/486 |
| 2003/0004562 A1 | 1/2003 | DiCarlo |
| 2003/0229388 A1 * | 12/2003 | Hayashi et al. .............. 623/1.1 |
| 2004/0199238 A1 * | 10/2004 | Brown et al. ................ 623/1.1 |

FOREIGN PATENT DOCUMENTS

| | | |
|---|---|---|
| EP | 0 897 690 A1 | 2/1999 |
| WO | WO 83/03348 | 10/1983 |
| WO | WO 98/29030 | 7/1998 |
| WO | WO 99/26530 | 6/1999 |
| WO | WO 00/32092 | 6/2000 |

* cited by examiner

ENDOVASCULAR GRAFT WITH PRESSOR AND ATTACHMENT METHODS

This application is a continuation-in-part of U.S. application Ser. No. 10/165,763, filed Jun. 7, 2002, now U.S. Pat. No. 7,261,733.

BACKGROUND OF THE INVENTION

This invention relates to the treatment of body lumens and, more particularly, to the endovascular placement of a prosthetic graft within vasculature for the purpose of repairing the same.

Ruptured abdominal aortic aneurysms (AAA) are a leading cause of death in the United States. Treatment options to repair AAA include conventional open surgery and implantation of an endovascular graft. Conventional open surgical repair of AAA involves major abdominal surgery with associated high rates of morbidity. Endovascular grafts have been developed to endoluminally bypass abdominal aortic aneurysms through minimally invasive surgery. Many patients that are unacceptable surgical risks for open repairs are eligible for endovascular graft implantation. Deployment of transfemoral, endovascular grafts to treat AAA is appealing for many reasons: avoidance of an abdominal incision, lack of aortic cross clamping, the potential for regional anesthesia, and a shortened hospital stay.

Untreated AAA have been shown to continue to expand until rupture, with an associated high mortality rate. Implantation of endovascular grafts have also been associated with high complication rates, including perioperative death, conversion to open repair, the need for further intervention, the need for hemodialysis, a failure to cure the AAA, and wound complications.

The inability to obtain or maintain a secure seal between the vessel wall and the endovascular graft is a complication unique to endovascular aneurysm exclusion. Because the term "leak" has been associated with aneurysm rupture following conventional surgery, the term "endoleak" has been proposed as a more definitive description of this complication. It is believed that persistent endoleaks result in continued aneurysm expansion, which may eventually lead to aneurysm rupture. Aneurysms that have been successfully excluded have shown a tendency towards a reduction in aneurysm diameter. Failure to properly exclude the aneurysm from systemic arterial blood pressure keeps the patient at risk of impending rupture. Endoleaks have been classified according to the source of the leaks. Current classifications of endoleaks include four categories. Type I endoleaks are "perigraft" or "graft-related" leaks that involve a persistent channel of blood flow due to inadequate or ineffective sealing at the ends of the endovascular graft, or between overlapping components of a modular system. Type II endoleaks are retrograde flow into the aneurysm sac from patent lumbar arteries, the inferior mesenteric artery, or other collateral vessels. Type III endoleaks result from fabric tears, graft disconnection, or graft disintegration. Finally, Type IV endoleaks are flow through the graft fabric associated with graft wall porosity or permeability. It has been recognized that preoperative patent side branches are not a good predictor of postoperative endoleaks.

There have been a number of reported cases of aneurysm rupture following implantation of an endovascular graft. Some of the ruptures occurred in patients without a documented endoleak.

A number of studies have focused on measurement of pressure within the aneurysm sac following implantation of an endovascular graft, both in the human patient, an animal model, or an in vitro model. Properly implanted endovascular grafts have been shown to reduce the pressure within the aneurysm sac while an endoleak, with or without detectable blood flow, continues to pressurize the sac at pressures equivalent to the systemic arterial pressure. Animal studies utilizing a predictable rupturing aneurysm model have shown that non-excluded aneurysms will rupture. Thrombosed aneurysm sacs may still receive pressurization from a sealed endoleak and this continued pressurization keeps the aneurysm at risk for rupture.

Current methods of patient follow-up include arteriography, contrast-enhanced spiral computed tomography (CT), duplex ultrasonography, abdominal X-ray, and intravascular ultrasound. All of these methods are costly and involve invasive procedures with associated morbidity that may need to be performed in a hospital. None of the imaging methods are completely successful in detecting endoleaks. Therefore, the potential exists for an endoleak to go undetected until eventual rupture. An increase in aneurysm diameter is detectable, and should be considered an indication of endoleak. To avoid aneurysm rupture an increase in aneurysm diameter must be detected in a timely fashion to identify patients in need of corrective endovascular procedures.

An endovascular graft with the ability to measure pressure within the aneurysm sac and provide feedback to the physician could provide acute confirmation of a procedure and identify those patients with persistent pressurization of their aneurysm, and subsequent risk of rupture. Some physicians are advocating that the follow-up examinations of AAA patients focus on pressure measurements, but that this is not currently clinically feasible. Furthermore, follow-up examinations may be performed in the physician's office as opposed to a hospital. Moreover, clinicians will have a new method to study the pathology of post-endovascularly treated AAA disease.

Accordingly, there exists a need for an endovascular graft that facilitates non-invasive measurement of pressure, as well as other pertinent parameters, within the aneurysm sac and along the endovascular graft itself as a means for confirming the success of a procedure as well as identifying patients at risk for aneurysm rupture after the endovascular graft is implanted.

However, providing devices on an endovascular graft to facilitate the measurement of pertinent parameters poses problems. The measurement device increases bulk, which can significantly effect the delivery profile of the endovascular graft and increase the force necessary to deploy the device, such as jacket or release wire retraction forces. Increased bulk is a significant issue for an endovascular graft. Furthermore, attachment of measurement devices to an endovascular graft may require sutures and the suture knots not only provide increased bulk, but are also potential graft wear points. Additionally, tissue growth around a measuring device attached to an implanted endovascular graft may interfere with its function and inaccurate data may result.

Another potential problem is the protection of a sensing device when it is attached to a medical device or during advancement of a medical device to an interventional site. In the situation where there exists the possibility of damaging a sensing device, measures must be taken to safely attach a sensing device or otherwise protect a sensing device attached to a medical device.

In a related matter, there exists a need to effectively and efficiently attach sensing or other devices to a medical apparatus. Whereas the art provides certain approaches to affixing such structure to medical apparatus, there is believed to be room for advancements in this area for particular applications.

The present invention addresses these problems and other needs.

SUMMARY OF THE INVENTION

Briefly and in general terms, the present invention is embodied in an endovascular graft with sensors attached thereto. The endovascular graft has the ability to be delivered endovascularly and measure pertinent parameters within the lumen in which it is implanted. The endovascular graft has the ability to transmit data about intra-lumen parameters to an external monitoring device. Confirmation of a successful implant procedure is quickly and easily obtained. Patient follow-up is less costly (conducted in the physician office), non-invasive, and more accurate, allowing prompt intervention in those patients most at risk for acute AAA rupture. The invention would also allow for more frequent patient follow-up, increasing the potential to diagnose and treat aneurysms at risk before acute rupture.

In one aspect of the invention, a modular endovascular graft having a main body component and one or more limb components is provided. One or more sensors are attached to the limb component(s). By attaching at least one sensor near the superior end of the limb component and sizing the main body component such that the sensor is adjacent to the aneurysm sac when the endovascular graft is implanted, measurement of pertinent parameters within the aneurysm sac is facilitated. The meaning of the term "adjacent" as used herein encompasses the sensor being located within the aneurysm sac or at a location where the parameters or properties being detected indicate conditions within the aneurysm sac. Measurements of pertinent parameters within the aneurysm sac may allow early confirmation of a successful procedure and identification of areas of the patient's vasculature at risk for aneurysm rupture, thrombus formation, infection, inflamation or other anomalies without the need for invasive procedures.

An antenna or other data transmitter and a power source also may be attached to the limb component adjacent to the aneurysm sac, allowing a physician or technician to monitor graft and vessel health without the need for an invasive procedure. The transmitter transmits measurements made by the sensors to a receiver located outside the patient's body. With the main body component unencumbered with sensors, transmitters or power sources, the bulk of the main body component is minimized and thereby, catheter diameter, jacket retraction and deployment complications are kept to a minimum.

In another aspect of the invention, an endovascular graft is provided that has attached thereto at least one integrated sensor/transmitter device capable of measuring a pertinent parameter and transmitting the measurements to an external monitoring device. Although having more bulk than a sensor, the integrated sensor/transmitter device has less total bulk than a sensor and independent transmitter device, thereby facilitating less total bulk for the endovascular graft.

Furthermore, the integrated sensor/transmitter device may be designed to allow one or more "satellite" sensors, having no function other than measurement, to be connected thereto. A single integrated sensor/transmitter device and smaller "satellite" sensors facilitate a smaller total bulk than multiple integrated sensor/transmitter devices. Attaching the integrated sensor/transmitter at a central location such as the graft crotch and "satellite" sensors at various locations on the endovascular graft facilitates measurement and transmission to an external monitoring device of pertinent parameters at multiple locations along the endovascular graft and within the lumen. The "satellite" sensors allow a complete profile of pertinent parameters to be obtained and may provide more accurate identification of anomalies. Measurement of pertinent parameters at multiple locations along the endovascular graft or within the aneurysm sac may allow early detection of a defective seal between endovascular graft components, graft wear or changes in aneurysm geometry. The smaller "satellite" sensors may also allow pertinent parameters to be measured from locations on the endovascular graft where local graft bulk is a constraint of the design, such as the graft contra limb or near the superior attachment system that holds the graft in the patient's aorta.

Additionally, it is contemplated that "satellite" sensors may be attached directly to the lumen of a patient. The integrated sensor/transmitter device also may be attached directly to the lumen or attached to an implanted endovascular graft.

Moreover, it is contemplated that passive devices, or monuments, which perform no sensing function may be attached to the implanted endovascular graft or directly attached to the aneurysm sac. By tracking the location of the monuments with a monitoring device, changes in the position of the endovascular graft within the lumen or changes in the geometry of the tissue outside the endovascular graft may be detected without the problems of encapsulation or thrombus isolation associated with the measurement of pertinent parameters. Such changes may provide early detection of endovascular graft displacement or aneurysm re-dilation due to an endoleak.

Sensors with pressure measurement capability may be used to detect pressure changes in the aneurysm sac indicative of graft failure or endoleak due to an inadequate seal between the endovascular graft and the vasculature. Sensors with temperature measurement capability may be used to detect temperature differentials associated with "hot spots" related to inflamation, infection or thrombus formation in the vessel. Sensors with the capability to measure oxygen and other blood constituents such as enzymes, proteins, and nutrients, may be used to detect minute blood flow indicative of endoleak. Sensors with the capability to measure electrical potential or magnetic fields may be used to detect differences in potential associated with areas of the vessel at risk for thrombus formation. Sensors also may be provided to facilitate other sensing applications such as blood oxymetry, blood glucose, blood or fluid flow, biochemical or hormonal balance, blood chemistry, positional data, dynamic displacement data, ocular pressure, respiration, electro physiology, tissue stress, venous return and body acoustics.

In yet another aspect of the invention, sensors are attached to an endovascular graft using one continuous suture. Starting at one location on the sensor, a running stitch around the sensor is used to attach the sensor to the graft fabric, thereby minimizing the number of knots necessary for attachment, in this case a single knot. It is contemplated that the running stitch may start at any location on the sensor depending on the location of the sensor on the endovascular graft. Minimizing the number of knots is advantageous because knots are potential graft wear points and add bulk. Additionally, a single knot attachment design may allow the sensor to be placed close to the graft crotch due to the lack of a knot at the end closest the crotch.

In an additional aspect of the invention, the sensors may be covered in a coating that either inhibits tissue growth or promotes a known or controlled amount and/or type of tissue growth. Because tissue growth may interfere with the ability of a sensor to perform its measurement function, inhibiting tissue growth or restricting tissue growth to a known type and/or amount may increase the reliability of measurements obtained.

In other aspects, there is provided methods for protecting sensing structure attached to medical devices. In one embodiment, the medical device can be folded during advancement to an interventional site to thereby provide temporary protection to delicate sensing devices. A specific approach is taken to attach the sensing device to a medical apparatus which provides a secure attachment while avoiding damage during fixation. Additional structure can be provided to aid in the handling of the sensing devices to further insure that the devices are not harmed.

Further methods and approaches for attaching a sensory device to a medical apparatus include employing patterns of adhesive tape or temporary affixing structure. Pockets can also be formed for receiving the sensing devices and holding them adjacent the medical apparatus. In other approaches, stitching patterns for affixing structures to medical devices are presented.

The invention is applicable to all applications of endovascular grafts to treat aneurysmal segments of blood vessels. Furthermore, the invention and methods disclosed herein may be applied any time it is desired to measure intra-luminal parameters in a non-invasive manner. It is contemplated that the invention may be used with all shapes of endovascular grafts known within the art.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

As shown in the exemplary drawings and for purposes of illustration, the invention is embodied in a prosthetic endovascular graft having the ability to measure pertinent parameters inside the lumen into which it is implanted and transmit the measurements to a receiver located external to the patient.

Figure 1:
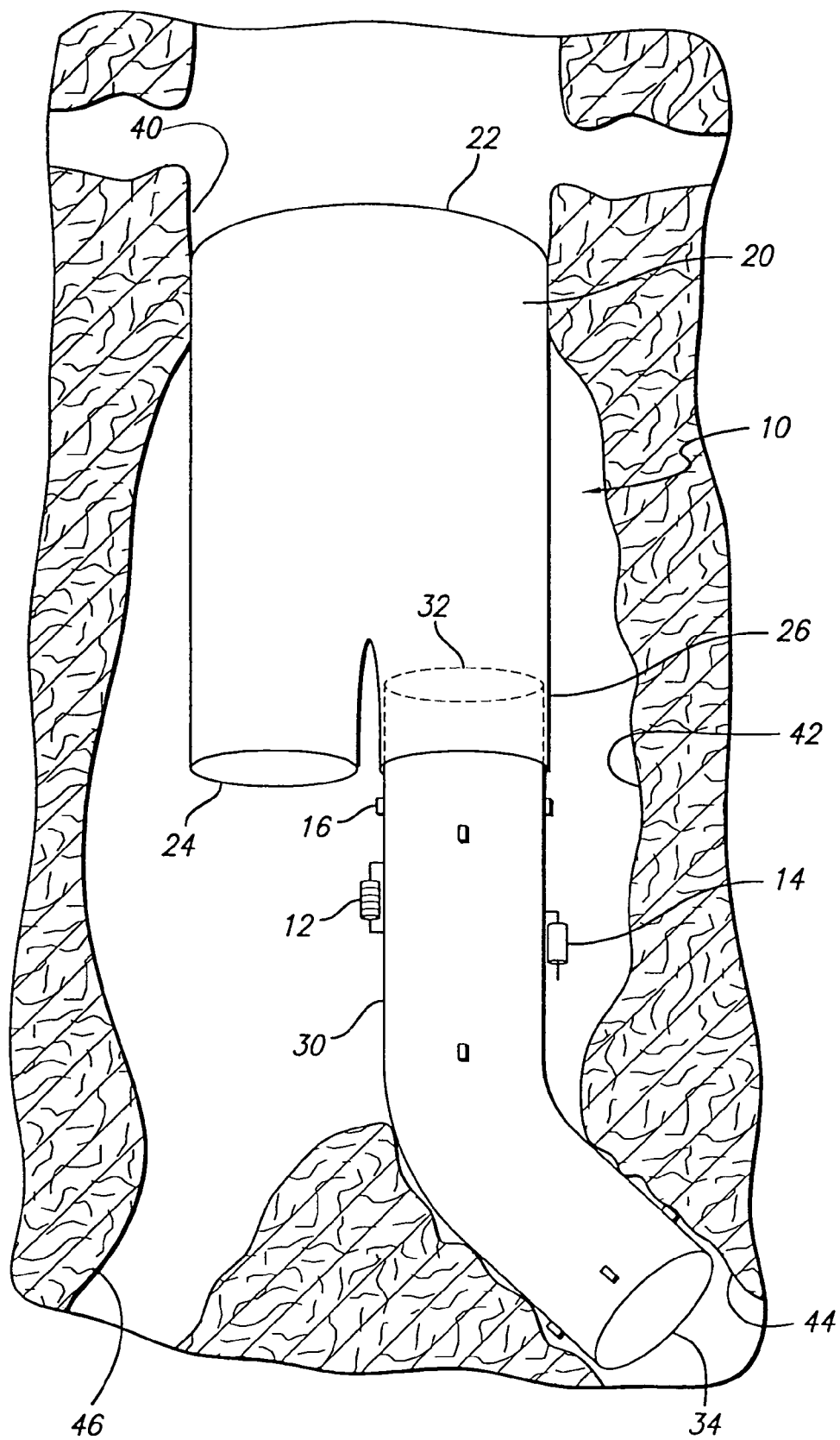
FIG. 1 is a partial cross-sectional view of one embodiment of the invention showing a partially assembled bifurcated endovascular graft implanted across an aneurysm sac.

Referring to FIG. 1, an embodiment of the invention is shown in which a modular bifurcated endovascular graft 10 of the type known within the art is implanted in a body vessel 40 across an aneurysm sac 42 in the area of the contra-lateral 44 and ipsi-lateral 46 iliac arteries using methods known within the art (only the contra-lateral limb is shown). The bifurcated endovascular graft 10 may be assembled in-vivo from a tubular trunk component 20 and two limb components 30. The trunk component 20 has a superior end 22 adapted to be secured above the aneurysm and an inferior end 24 adapted to accept the limb components 30. The limb component 30 has a transmitter 12, power source 14, and sensors 16 attached external the graft material. The transmitter 12, power source 14 and sensors 16 can be integrated into one device as described below. The limb component 30 has a superior end 32 adapted to mate with the trunk component 20 inferior end 24 and an inferior end 34 adapted to be secured to the contra-lateral 44 iliac artery.

The sensors 16 measure pertinent parameters outside the endovascular graft 10 and the power source 14 provides power for the transmitter 12 which transmits the measurements to a receiver (not shown) located outside the patient's body. The transmitter 12, power source 14 and receiver (not shown) may be of any type known in the art of surgical implants or other systems utilizing miniaturized power sources and transmitters. The power source 14 and transmitter 12, for example, may be of the type used in pacemaker technology or passive power sources such as ultrasonic chargeable capacitors.

One or more sensors 16 are located near the superior end 32 of the limb component 30 but inferior the attachment/sealing area 26 between the trunk component 20 and limb component 30 such that the seal between the trunk component 20 and limb component 30 is not jeopardized. Note that the attachment/sealing area 26 is such that one or more of the sensors 16 on the limb component 30 is adjacent the aneurysm sac 42, thereby facilitating measurement of pertinent parameters within the aneurysm sac 42 without encumbering the trunk component 20 with sensors 16. Note also that the transmitter 12 and power source 14 are attached to the limb component 30 such that they are also adjacent the aneurysm sac 42. Minimizing the bulk of the trunk component facilitates a smaller delivery profile for the endovascular graft 10.

The sensors 16 may measure pressure, with the measurements used as an aid in endovascular graft 10 placement or to identify anomalies that occur after endovascular graft 10 implantation but before aneurysm rupture occurs. The sensors 16 may detect changes in pressure resulting from blood leakage between the endovascular graft 10 and the vessel wall 40, an endoleak resulting from an inadequate seal between them. Furthermore, the sensors 16 may detect changes in pressure resulting from leakage from an endoleak between the trunk 20 and vessel wall 40. Because sensors 16 are located in the area of the aneurysm sac 42, there may be multiple sensors 16 disbursed over the graft material outer wall since local thrombus or calcification may shield one or more of the sensors 16 from blood flow and render their measurements erroneous. Moreover, the sensors 16 may allow pressure differences throughout the "excluded" aneurysm sac 42 to be mapped. It is contemplated that pressure measurements in the aneurysm sac may be obtained to an accuracy range of +/−1 to 30 mm Hg and preferably of +/−10 mm Hg.

Alternatively, the sensors 16 may measure temperature. Differences in temperature may identify "hot spots" associated with infection, inflammation, thrombus formation or other anomalies that indicate an increased risk for aneurysm rupture. Methods known in the art of pathology and physiology may be used to relate temperature to changes in the vessel walls within which the endovascular graft is implanted.

Alternatively, the sensors 16 may detect blood flow by measuring oxygen or other constituents, such as enzymes, proteins and nutrients, which are altered by the presence of blood flow. Such sensors may allow detection of minute blood flow, often missed by conventional imaging modalities, and, therefore, allow endoleaks to be detected earlier. One method is to obtain a baseline of the constituents upon implantation of the endovascular graft. Thereafter, changes in the amount of the measured constituents may be used to identify anomalies.

Alternatively, the sensors 16 may measure electrical potential or magnetic field strength. Changes in electrical potential may identify areas of the patient's vasculature that are at risk for thrombus formation. Induced magnetic fields indicate motion at a charged portion of the aneurysm such as would occur from pulsatile pressure.

Sensors also may be provided to facilitate other sensing applications such as blood oxymetry, blood glucose, blood or fluid flow, biochemical or hormonal balance, blood chemistry, positional data, dynamic displacement data, ocular pressure, respiration, electro physiology, tissue stress, venous return and body acoustics.

Although shown external the limb component 30 in FIG. 1, it is contemplated that the transmitter 12, power source 14 and sensors 16 may be located internal the graft material of the limb component 30. It is further contemplated that the number of transmitters 12, power sources 14 and sensors 16 shown in FIG. 1 may be varied to meet the requirements of the individual patient. It is further contemplated that sensors 16 which measure different pertinent parameters may be used together. Moreover, the invention shown in FIG. 1 may be utilized in any type of endovascular graft implant known in the art.

Figure 2:
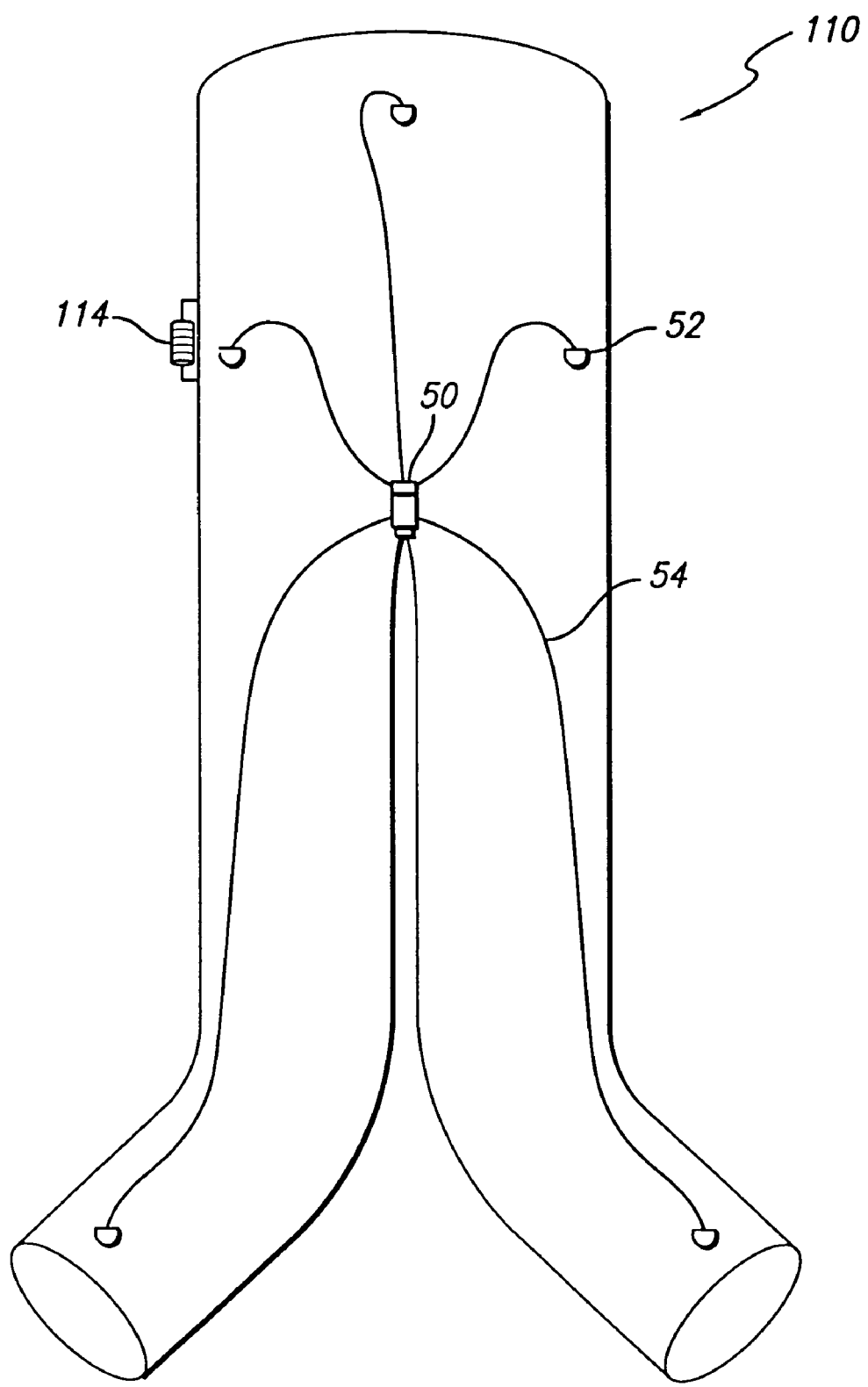
FIG. 2 is a perspective view of another embodiment of the present invention showing a bifurcated graft with an integrated sensor/transmitter device and "satellite" sensors.

Referring to FIG. 2, another embodiment of the invention is shown in which an integrated sensor/transmitter 50 is attached to the endovascular graft 110 and "satellite" sensors 52 are attached at various locations on the endovascular graft 110. The integrated sensor/transmitter 50 is capable of measuring a pertinent parameter as well as transmitting measurements to a receiver (not shown) outside that patient's body. The "satellite" sensors 52 only measure pertinent parameters and their measurements are transmitted by the integrated sensor/transmitter, to which they are connected by leads 54. The "satellite" sensors 52 may provide a complete profile of pertinent parameters over the surface of the endovascular graft 110 and, therefore, facilitate better identification of anomalies.

Because the "satellite" sensors 52 are smaller than the integrated sensor/transmitter 50, the overall bulk of the endovascular graft 110 is smaller than if multiple integrated sensor/transmitter devices 50 were utilized. Furthermore, the smaller "satellite" sensors 52 may be placed such that measurements may be obtained from multiple locations, such as near the superior attachment area or within the aneurysm sac 42. Moreover, the smaller "satellite" sensors 52 facilitate measurements from places on the endovascular graft 110 where local graft bulk is a constraint of the design, such as the contra limb, or near the superior attachment system that holds the graft in the patient's aorta.

A separate power source 114 may be provided. The power source can be integrated into the sensor/transmitter as described previously and further below. The leads 54 which connect the integrated sensor/transmitter 50 to the "satellite" sensors 52 may be woven into the graft fabric or attached external to the endovascular graft 110.

It is contemplated that the location and number of integrated sensor/transmitter devices 50, power sources 114 and "satellite" sensors 52 shown in FIG. 2 may be varied to meet the requirements of the individual patient. In the embodiment shown, the integrated sensor/transmitter device 50 is located at the crotch, thereby allowing it to be near the center of the aneurysm sac 42 (see FIG. 2) while still being located furthest away from the aneurysm wall during shrinkage. It is further contemplated that the invention shown in FIG. 2 may be utilized in any type of endovascular graft implant known in the art.

Moreover, the integrated sensor/transmitter 50 and "satellite" sensors 52 may be of any type known in the art used to measure pressure, temperature, oxygen and other blood constituents, electrical potential or any other pertinent parameter indicative of endovascular graft or lumen health. One such integrated sensor/transmitter 50 to measure pressure is disclosed in U.S. Pat. Application Publication No. 2002/0045921 (Wolinsky et al.), the contents of which are hereby incorporated by reference. Again, other sensing applications may be supported such as blood oxymetry, blood glucose, blood or fluid flow, biochemical or hormonal balance, blood chemistry, positional data, dynamic displacement data, ocular pressure, respiration, electro physiology, tissue stress, venous return and body acoustics.

Figure 3:
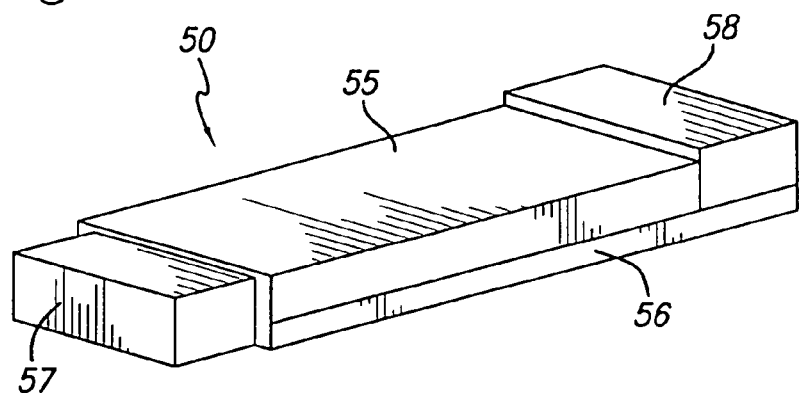
FIG. 3 is a perspective view of a typical integrated sensor/transmitter device of the present invention.

FIG. 3 shows a typical integrated sensor/transmitter 50 for use with the present invention. The integrated sensor/transmitter 50 includes a control chip 55 with a transmitter/receiver, energy exchanger 56, capacitor 57 and sensor 58. An external receiver (not shown) may contain a transducer, computer, LCD display and measurement display devices, such as barometers if the sensor 58 measures pressure. In operation, the transducer in the external receiver charges the capacitor 57 using ultrasonic energy and activates the sensor 58 to measure a pertinent parameter and ultrasonically transmit the measured parameter. The external receiver receives the transmitted pertinent parameter, assesses the measurement and displays the measurement, for example, as a pressure pulse curve.

Figure 4:
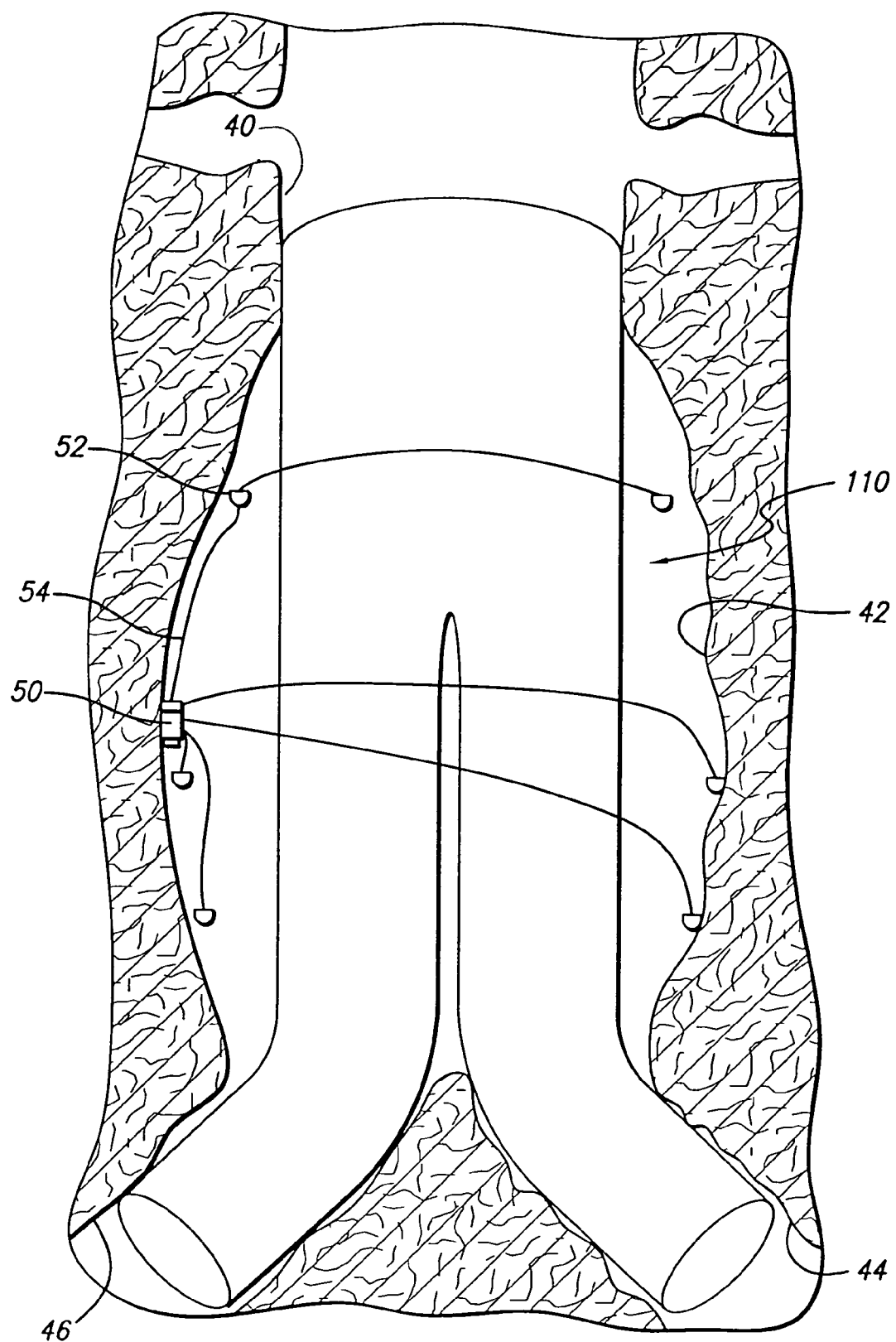
FIG. 4 is a partial cross-sectional view of an alternate embodiment of the invention shown in FIG. 2 showing a bifurcated graft implanted across an aneurysm sac into which an integrated sensor/transmitter device and "satellite" sensors have been attached.

Although FIG. 2 shows an integrated sensor/transmitter 50 and "satellite" sensors 52 connected by leads 54 and attached to the endovascular graft 110, alternate embodiments of the invention may utilize an integrated sensor/transmitter 50 as the sole implant. Furthermore, the "satellite" sensors 52 may be attached to the vessel 40 with the integrated sensor/transmitter 50 either attached to the vessel 40 or attached to the endovascular graft 110. FIG. 4 shows an endovascular graft 110 implanted across an aneurysm sac 42 into which an integrated sensor/transmitter 50 connected to "satellite" sensors 52 by leads 54 have been attached. It is contemplated that pressure measurements in the aneurysm sac 42 may be obtained to an accuracy range of +/−1 to 30 mm Hg and preferably +/−10 mm Hg utilizing either an integrated sensor/transmitter 50 alone or in conjunction with one or more "satellite" sensors 52 or integrated sensor/transmitters 50.

In an alternate embodiment of the invention illustrated in FIGS. 2 and 4, micro devices having the capability to sense their location relative to each other are either attached to the endovascular graft 110 or attached to the vessel 40. The micro devices may be excited by an external energy source, sense their relative location and transmit the data to a receiver located outside the patient's body. The data may then be interpreted to determine if displacement of the endovascular graft 110 or changes in the geometry of the vessel 40 has occurred. Such changes may provide early detection of endovascular graft 110 displacement or aneurysm 42 re-dilation due to an endoleak. Additional micro devices could be provided for better resolution. Detecting location of the micro devices rather than measuring a pertinent parameter minimizes reliability problems due to encapsulation or thrombus isolation. It is contemplated that the micro devices may be an ultrasonic crystal attached or integral to a MEM chip having the ability to read, interpret and transmit data. The micro devices also may be ultrasonic or other energy reflectors utilized in conjunction with an energy source. Using ultrasound to show or image reflector location would be much easier than creating an ultrasound image of the tissue.

Figure 5:
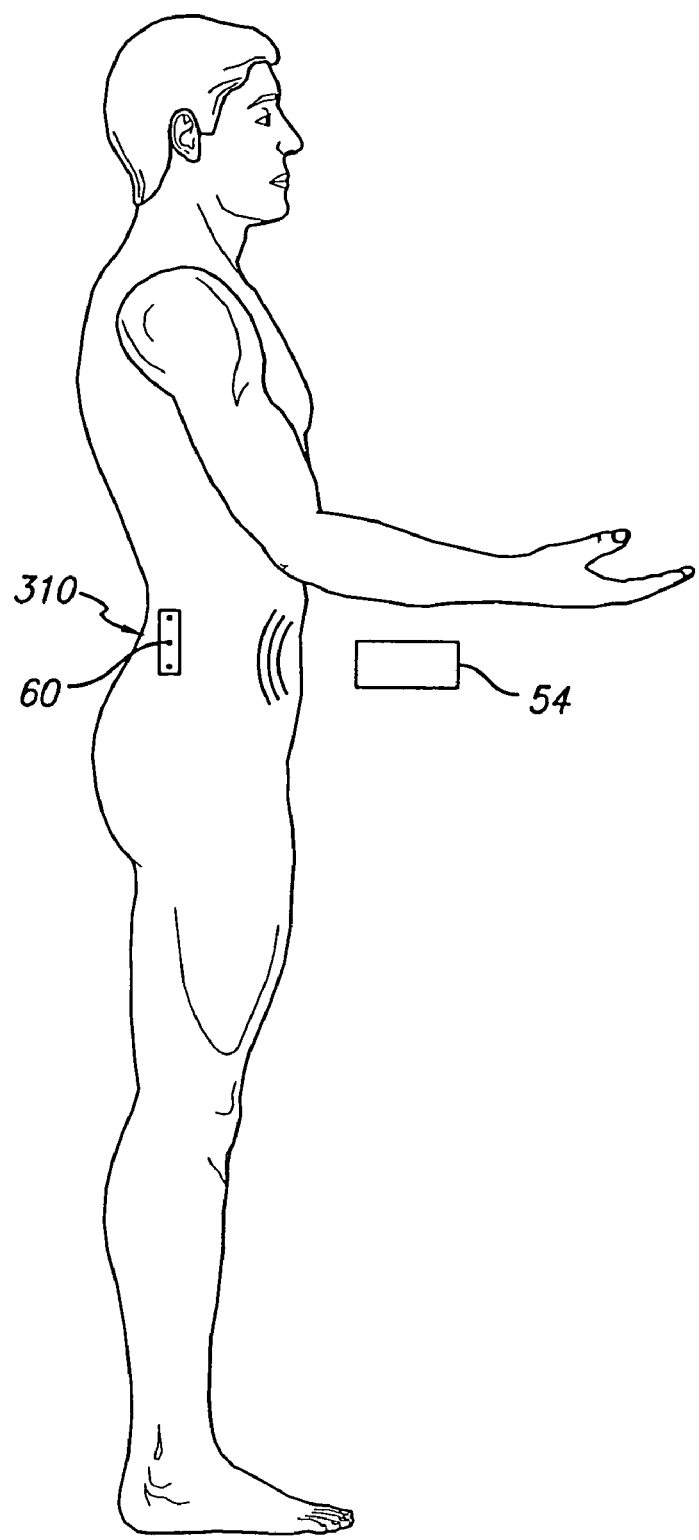
FIG. 5 is a schematic view of another embodiment of the present invention showing an endovascular graft with monuments attached thereto implanted in a patient's body and an external source/receiver.

In a further embodiment of the invention illustrated in FIGS. 2 and 4, devices or monuments which perform no sensing function may be attached to the implanted endovascular graft 110 or directly attached to the aneurysm sac 42. The location of the monuments may be tracked with a monitoring device to detect changes in the position of the endovascular graft 110 within the vessel 40 or changes in the geometry of the tissue outside the endovascular graft 110. It is contemplated that the monitoring device may be located external the patient's body or attached to an implanted endovascular graft. FIG. 5 illustrates an external monitoring device 54 being used to sense the location of an endovascular graft 310 having monuments 60 attached thereto which has been implanted in a patient's body. It is contemplated that the monuments may be electrically passive devices or magnetic sensors. The use of RF or magnets to sense the position of monuments is contemplated.

In one example, the position of magnetic sensors attached to the aneurysm sac 42 are measured using an external magnet of known magnetic field strength and shape. By moving the external magnet to multiple positions and orientations outside the body and polling the magnetic sensors with ultrasound, a baseline of magnetic sensor positions is established. Subsequent polling of the magnetic sensor positions allows changes in aneurysm sac 42 geometry to be detected.

Figure 6:
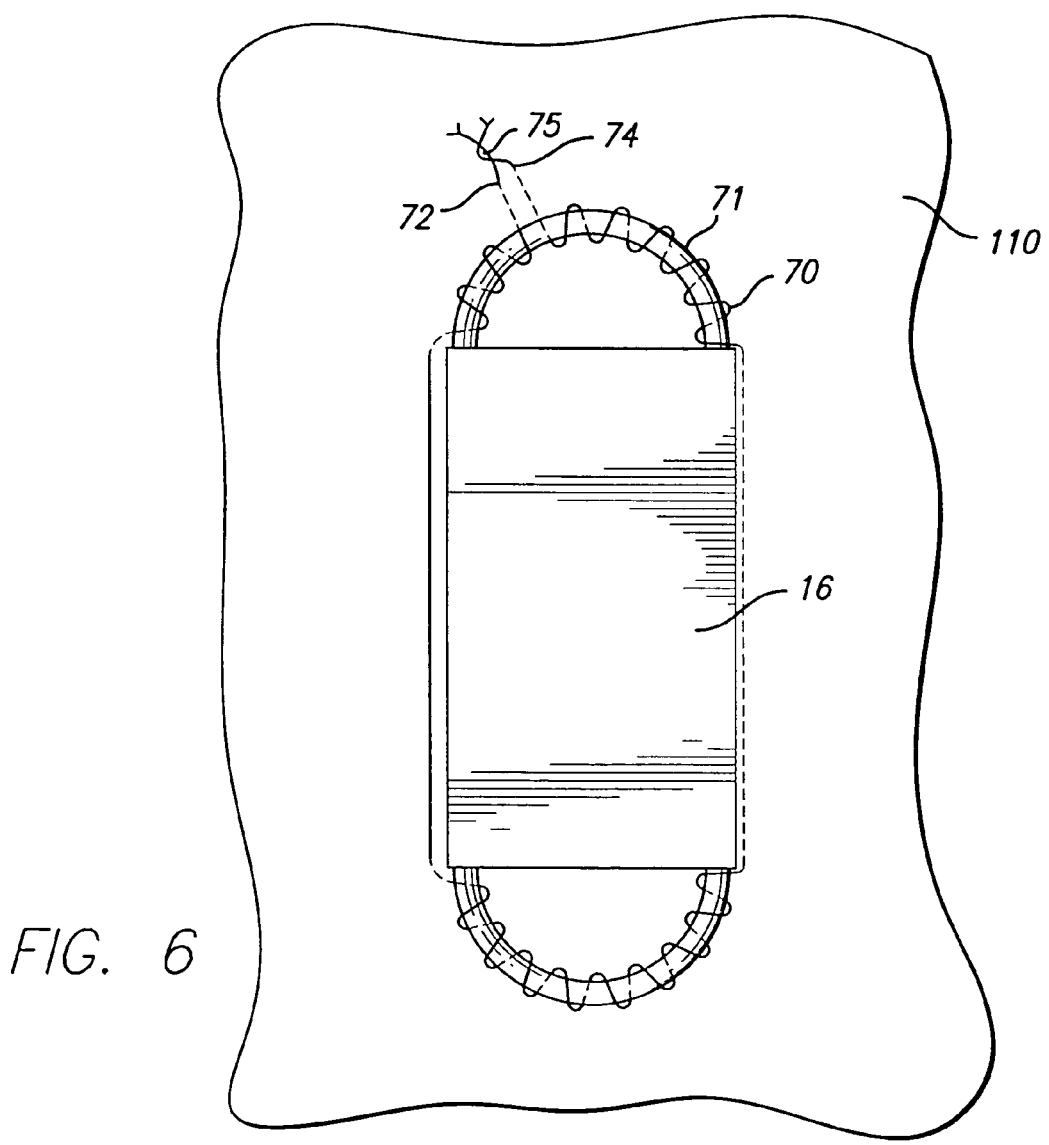
FIG. 6 is an enlarged view of a portion of graft fabric showing a sensor of the present invention attached using a single suture and running stitch.

In yet another embodiment of the invention shown in FIG. 6, sensors 16 or integrated sensor/transmitters 52 are attached to the endovascular graft 110 fabric using one continuous suture 70 with a running stitch, from a starting point 72 on sensor 16, which continues around the sensor 16 and back to an end point 74 (the dashed lines in FIG. 6 indicate where the suture 70 is on the inner diameter of the endovascular graft 110 fabric). Suture loops 71 are provided on the sensor 16 to facilitate attachment. A single knot 75 may be used to join the ends of the suture 70. It is contemplated that the running stitch may start and end at either end of the sensor and utilize more or less stitches depending on the location of the sensor 16 on the endovascular graft 110 and the attachment requirements. Minimizing the number of knots not only reduces bulk but also reduces potential graft wear points and may allow the sensor to be placed close to the graft crotch due to the lack of a knot at the distal end. It is further contemplated that the continuous suture 70 attachment method may be utilized with sensors 16 having suture holes or any other attachment mechanism.

In yet another embodiment of the invention, the sensors 16 may be covered in a coating, such as Teflon or heparin, to inhibit tissue growth or covered in a coating, such as Thrombin, to promote a known or controlled amount of tissue growth. Inhibiting or controlling tissue growth, which may interfere with performance, increases the reliability of the measurements made by the sensors 16.

Figure 7:
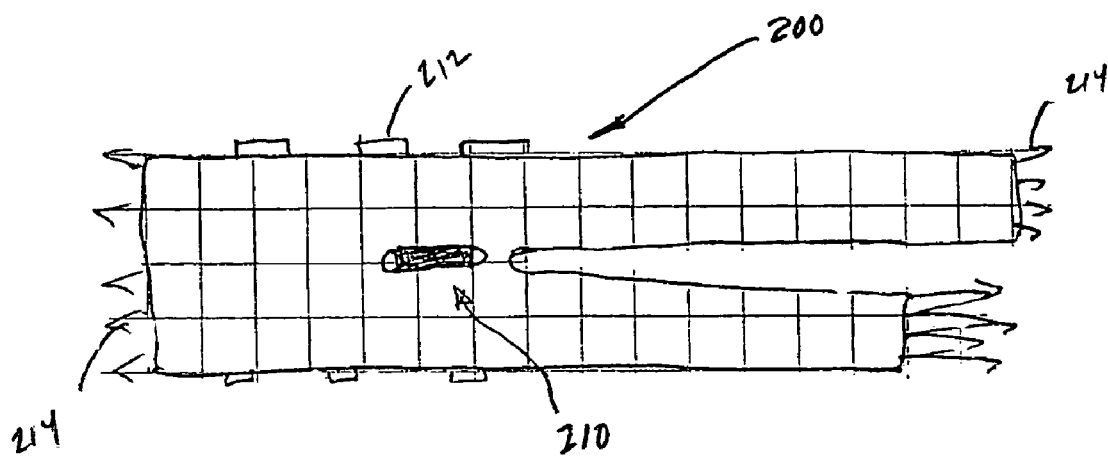
FIG. 7 is a side view, depicting a graft with a sensor attached thereto.
Figure 8:
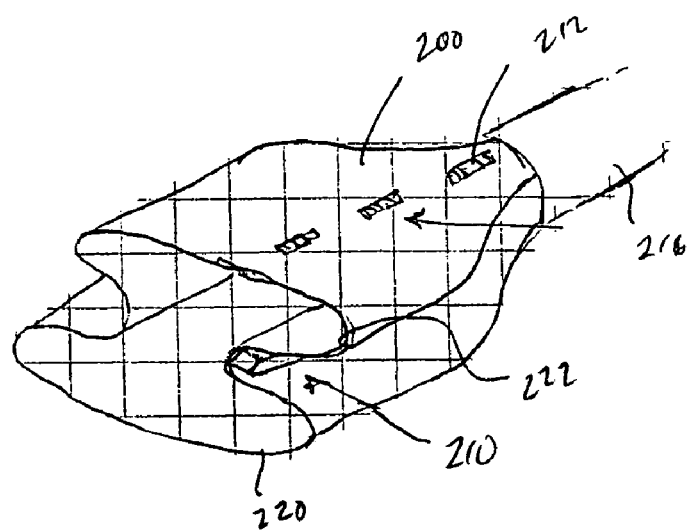
FIG. 8 is a partial perspective view, depicting the graft of FIG. 7 folded in an H-configuration.

With reference to FIGS. 7 and 8, there is shown a typical medical device in the form of a graft 200 for use in interventional procedures such as aortic aneurysm repair. For any of the previously discussed reasons, the graft 200 can be equipped with a sensing or other device 210. Radiopaque markers 212 can also be attached to the graft as well as stents 214 or other frames or anchoring devices. In a situation where there is an interest in protecting the sensing device 210 during advancement of the graft 200 to an interventional site, using a delivery catheter 216, the graft 200 can be initially folded in a generally H-shaped configuration, such that the sensor 210 is placed between a pair of folds 220, 222 in the graft 200. As the delivery catheter 216 is drawn over the graft 200 and sensor 210, the graft itself acts as a protection barrier.

Figure 9:
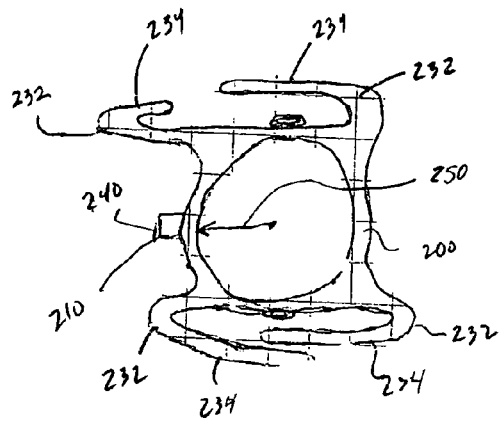
FIG. 9 is an end view, depicting a first step in folding material of the graft of FIG. 8 about the sensor.
Figure 10:
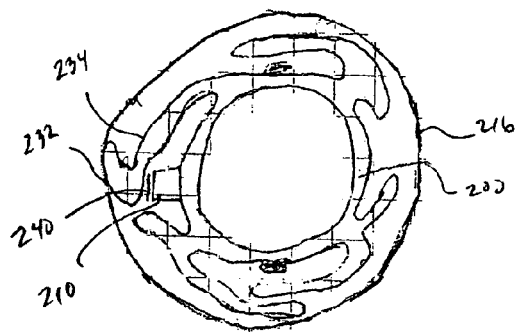
FIG. 10 is an end view, depicting a second step in folding material of the graft of FIG. 8 about the sensor.
Figure 11:
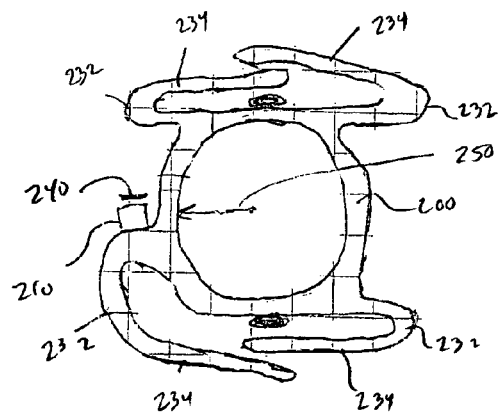
FIG. 11 is an end view, depicting a first step of a second approach to folding material of the graft of FIG. 8 about the sensor.
Figure 12:
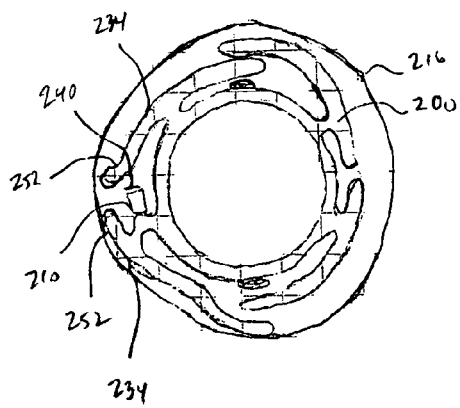
FIG. 12 is an end view, depicting a second step of a second approach to folding material of the graft of FIG. 8 about the sensor.

Various approaches can be taken to protect a sensing device 210. For example, as shown in FIGS. 9 and 11, after folding the graft into an H-configuration, a second fold 232 is placed in legs 234 of the H-shape. Where a membrane 240 of a sensor 210 is oriented generally perpendicularly to a radius 250 of the tubular graft device 210 (See FIGS. 9 and 10), one folded leg 234 is placed over the membrane 240 thereby providing a double layer of protection for the sensor 210 when placed within a delivery catheter 216. Alternatively, as shown in FIGS. 11 and 12, where the sensor membrane 240 is generally parallel to a graft radius, folded portions 252 of two legs 234 can be configured over the sensor 210 for protection where the graft 200 is loaded within a catheter 216.

Figure 13:
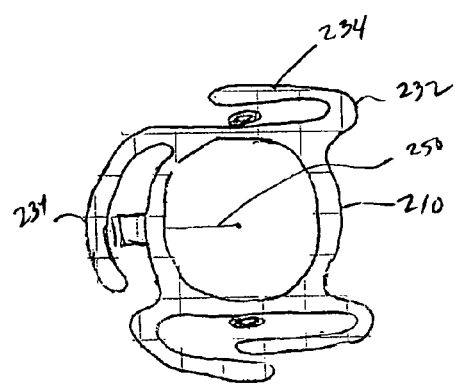
FIG. 13 is an end view, depicting a third approach to folding material about a sensor.

In either approach, the fragile membrane 240 of a sensor 210 is protected from trauma and wear during loading within a catheter 216 as well as advancement within vasculature. Moreover, the sometimes fragile membrane 240 is therefore only exposed upon deployment at an interventional site. Such an approach can ensure that the sensor is fully operational when implanted at an interventional site. In a related approach (See FIG. 13), instead of using two folded sections to protect a sensor or otherwise placing a second fold 232 within a leg 234, a leg 232 can be directly placed over a sensor for protection. Other folding approaches can also be employed for protection.

Figure 15:
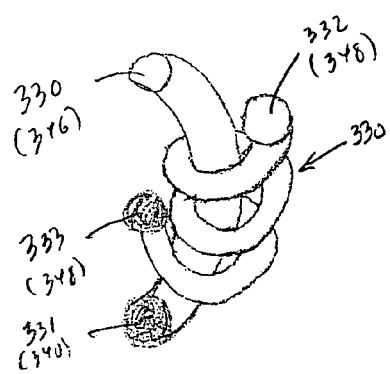
FIG. 15 is an enlarged view, of a knotting technique.
Figure 14:
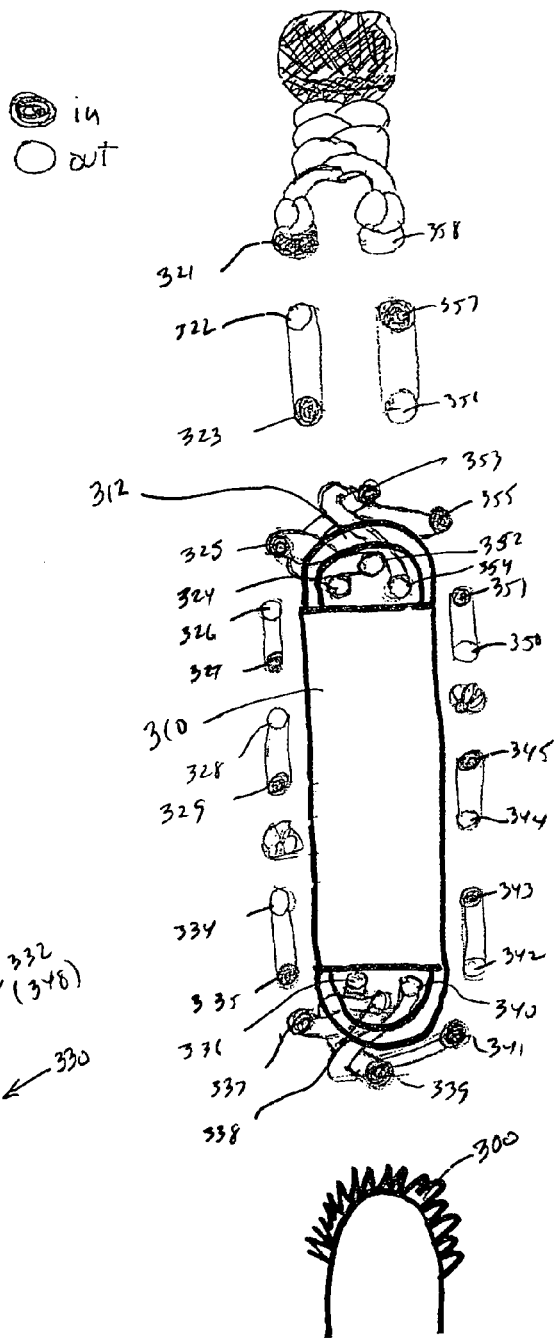
FIG. 14 is a side view, depicting an approach for affixing a sensor to a medical device.

Turning now to FIGS. 14 and 15, there is shown an approach for attaching a sensor 310 with looped ears 312 to a graft. In the FIGS., dark end circles represent stitching entering a graft wall and open circles represent stitching exiting a graft wall. In one particular approach, sensor lower stitches are located approximately 1 mm from flow divider stitching 300 such as that found in a bifurcated graft. Initially, the sensor 310 is tacked in place with a few simple stitches, and no knots. With a new piece of suture, an overhand knot is made about 3 cm from the end of the suture. A needle is inserted into the graft (at 321) approximately 16 to 17 mm away from the flow divider 300 and re-inserted from the inside so that it comes out (at 322) 1.0 to 1.5 mm closer to the flow divider 300 and is pulled snug. The needle is then inserted into the graft (at 323) 1 mm closer to the flow divider 300, and exits the graft (at 324) through the sensor ear 312 (stitch points 323 and 324). Care is taken to not damage the sensor membrane. Next, the needle is inserted into the graft over the sensor ear 312 at stitch point 325, close to the sensor ear 312 and out near the side of the sensor 310, at stitch point 326 and the suture is again pulled snug.

A running stitch is then made by inserting the needle into the graft at stitch point 327 and out at stitch point 328. Spacing of about 1.5 mm is used. Following that, a second running stitch is then made by inserting the needle into the graft at stitch point 329, about 1.5 mm away and out at stitch point 330, about 0.5 mm away and pulling the suture snug. As shown in greater detail in FIG. 15, a double loop knot is formed by inserting the needle into the graft 1 mm away at point 331, reversing direction to come out at point 332, which is half way between points 330 and 331. The stitch at point 330 to point 331 is left loose. The needle is wrapped twice around the loose stitch and then pulled snug. The needle is inserted into the graft (point 333) half way between points 330 and 331, but on the opposite side of the stitch from point 332 and again pulled snug. This forms a knot.

Thereafter, the suture is directed to come out at point 334, about 0.5 mm from the double loop knot. The needle is inserted into the graft 1.5 mm away, at point 335 and pulled snug. The suture is routed through the graft inside the sensor ear 312 at stitch point 336. The needle is inserted into the graft over the sensor ear 312 at stitch point 337, close to the sensor ear 312. The suture is directed up through the graft inside the sensor ear 312 at stitch point 338. Stitch points 336, 338, 340 made inside the sensor loop are approximately 2 to 3 warps or wefts apart.

Further stitches are made to hold the sensor ear. First, the needle is looped around stitch 336-337, then inserted over the sensor ear stitch point 339, close to the sensor ear. The needle then is passed through the graft inside the sensor ear at stitch point 340. A loop is placed around stitch 338-339, then over the sensor ear at stitch point 341, close to the sensor ear.

A running stitch is then created. Near the side of the sensor, the suture is routed out of the graft at stitch point 342 and pulled snug. The needle is then inserted into the graft at stitch point 343, about 1.5 mm away, and out at stitch point 344, about 1.5 mm away. A second running stitch is made by inserting the needle into the graft at stitch point 345, about 1.5 mm away and out at stitch point 346, about 0.5 mm away. The suture is again pulled snug.

A double loop knot is formed by inserting the needle into the graft 1 mm away at point 347 and reversing direction to come out at point 348, which is half way between points 346 and 347. This stitch 346 to 347 is left loose. The needle is then wrapped twice around the loose stitch and pulled snug. Next, the needle is inserted into the graft (point 349) half way between points 346 and 347, but on the opposite side of the stitch from point 348 and pulled snug.

The last running stitch on this side of the sensor is made by routing the needle out at point 350, about 0.5 mm from the double loop knot. The needle is then inserted into the graft 1.5 mm away at point 351 and advanced up through the graft inside the sensor ear at stitch point 352 and pulled snug.

To make the stitches that hold the sensor ear, the needle is looped around stitch 324-5, then inserted over the sensor ear at stitch point 353, close to the sensor ear. The needle is then placed up through the graft inside the sensor ear at stitch point 354. Next the needle is looped around stitch 352-33, then inserted over the sensor ear at stitch point 355, close to the sensor ear. Stitch points 324, 352, 354 made inside the sensor loop are approximately 2 to 3 warps or wefts apart.

The foregoing approach is intended to provide a secure and effective attachment of the sensor 310 to a graft. Moreover, the described approach minimizes potential damage during the attachment process as the sensing device is only engaged at the looped ears 312 and away from more fragile portions of the sensor 310.

Figure 16:
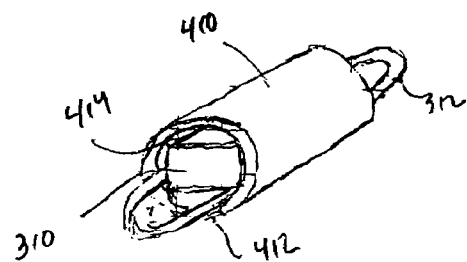
FIG. 16 is a perspective view, depicting a first embodiment of structure for handling and protecting a sensing device.
Figure 17:
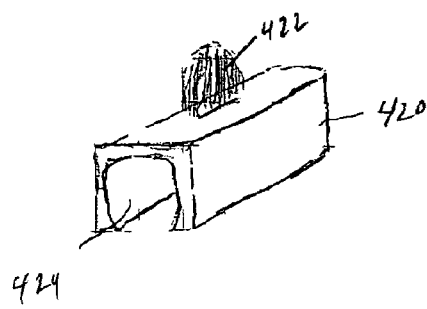
FIG. 17 is a perspective view, depicting a second embodiment of structure for handling and protecting a sensing device.
Figure 18:
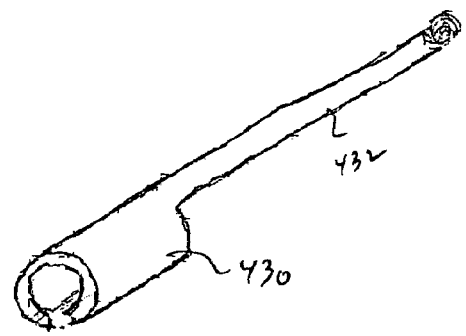
FIG. 18 is a perspective view, depicting a third embodiment of structure for handling and protecting a sensing device.

With reference to FIGS. 16-18, apparatus for handling delicate sensing devices are shown. In a first embodiment, a tubular apparatus 410 including a longitudinal slit 412 and an internal bore 414 sized for receiving a sensing device 310 with looped ears 312 can be employed for handling. The tubular apparatus includes a body that has sufficient rigidity to protect the sensor 310 during transporting the sensor to a medical device for attachment thereto. The tubular apparatus can then be removed before or after the sensor is secured to the medical device.

In other aspects, a handling device can be embodied in a generally rectangular structure 420 including a grasping wing 422 projecting from an exterior of the apparatus and a slotted interior 424 sized for receiving a sensing or other fragile device. The handling device can also be embodied in a tubular receiver 430 including a handle 432 extending longitudinally from a side wall. Both such structures are again intended for handling sensitive devices and for possibly holding the devices during attachment to a medical or other device or during placement of graft folds shown in FIGS. 9-13.

Figure 19:
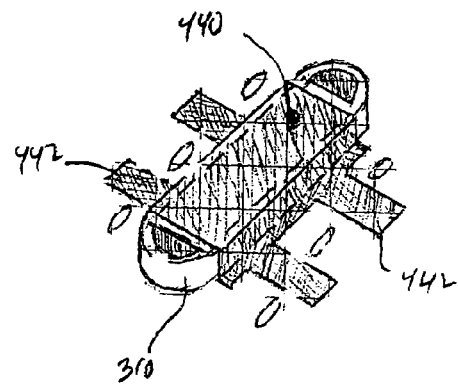
FIG. 19 is a perspective view, depicting a first embodiment of structure for aiding in affixing a sensing device to a medical apparatus.
Figure 20:
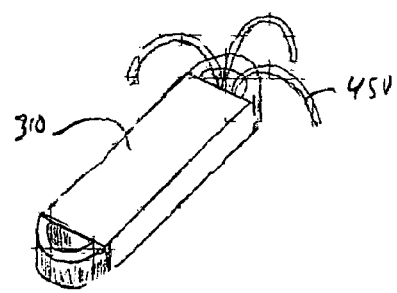
FIG. 20 is a perspective view, depicting a second embodiment of structure for aiding in affixing a sensing device to a medical apparatus.

Turning now to FIGS. 19 and 20, there are shown two further approaches for aiding in attaching sensors 310 to a graft or other medical device. An adhesive strip 440 with multiple wings 442 can be sized to temporarily or permanently overlap a sensor 310. The wings 442 are designed to provide space for auxiliary attaching mechanisms to gain access to the medical device and to facilitate for example, the sewing of the sensors to the medical device. Thus, the looped ears 312 of a sensor 310 are accessible. In another approach, hooked members 450 can be employed to temporarily attach a sensor to a medical apparatus so that permanent means can be utilized in the affixation process. It is also contemplated that glue or other adhesive can be applied to an underside of the sensor 310 to hold it in place during an affixation process. These approaches as well as aspects of previous approaches also can be used to temporarily attach a sensor to a graft until the assembly is deployed within vasculature at which time the handling or protective device is removed. Dissolving material or release wires and the like can be used to disengage and remove the sensor handling or protective structure.

Figure 21:
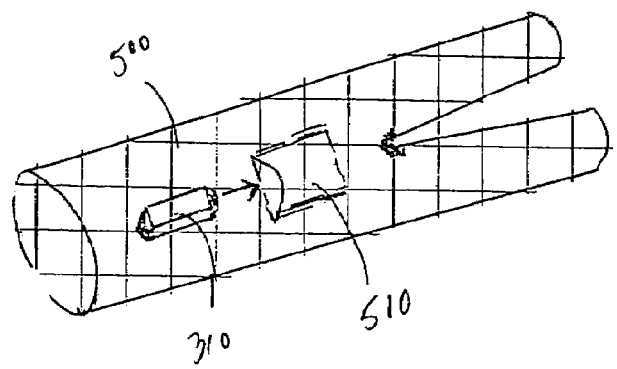
FIG. 21 is a perspective view, depicting a graft with a first embodiment of structures for receiving a sensing device.
Figure 22:
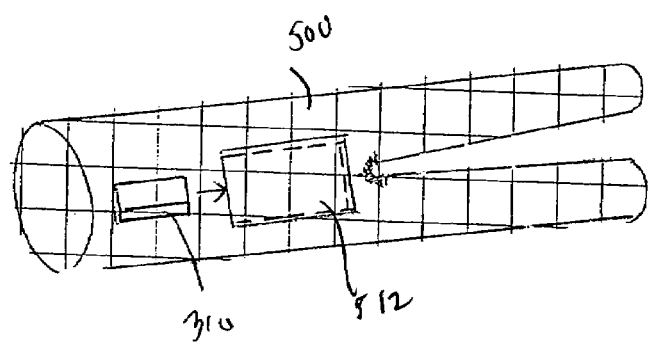
FIG. 22 is a perspective view, depicting a graft with a second embodiment of structures for receiving a sensing device.
Figure 23:
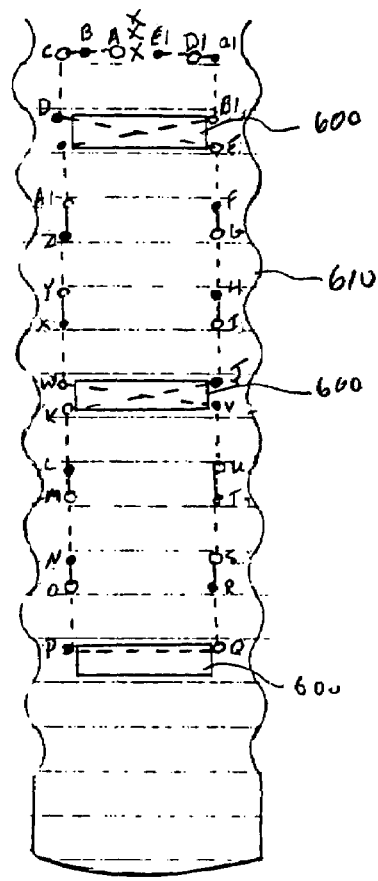
FIG. 23 is a side view, depicting a first sewing pattern for attaching devices to a graft.
Figure 24:
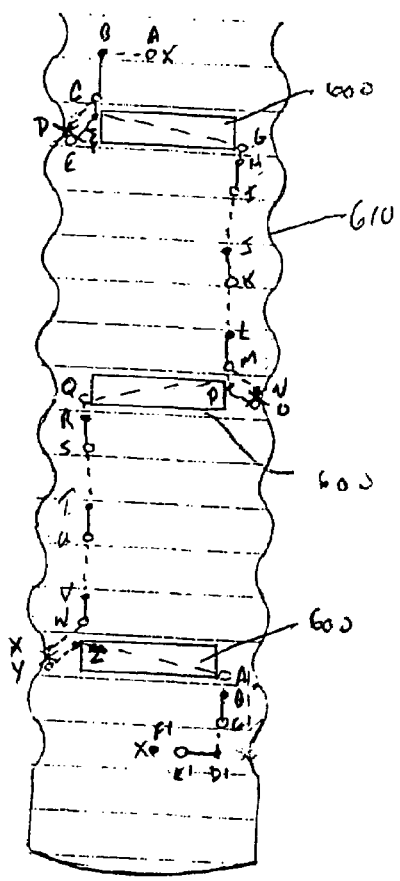
FIG. 24 is a side view, depicting a second sewing pattern for attaching devices to a graft.
Figure 25:
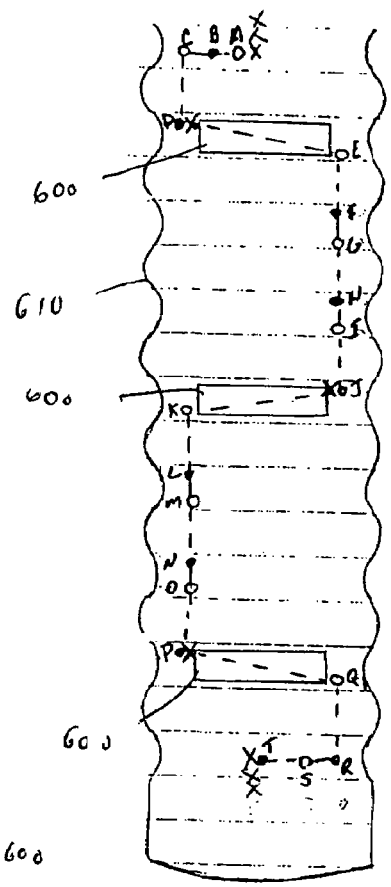
FIG. 25 is a side view, depicting a third sewing pattern for attaching devices to a graft.
Figure 26:
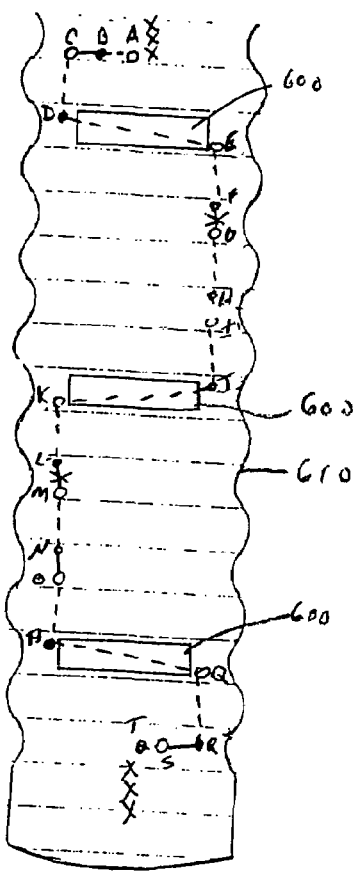
FIG. 26 is a side view, depicting a fourth sewing pattern for attaching devices to a graft.
Figure 27:
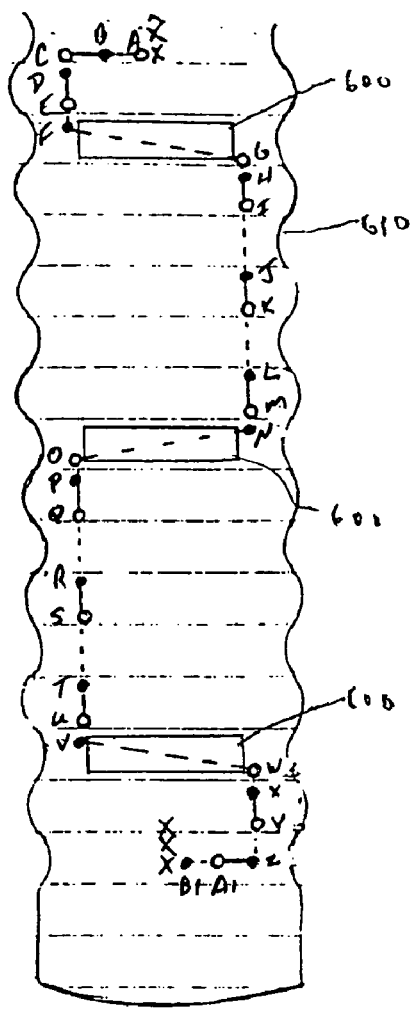
FIG. 27 is a side view, depicting a fifth sewing pattern for attaching devices to a graft.
Figure 28:
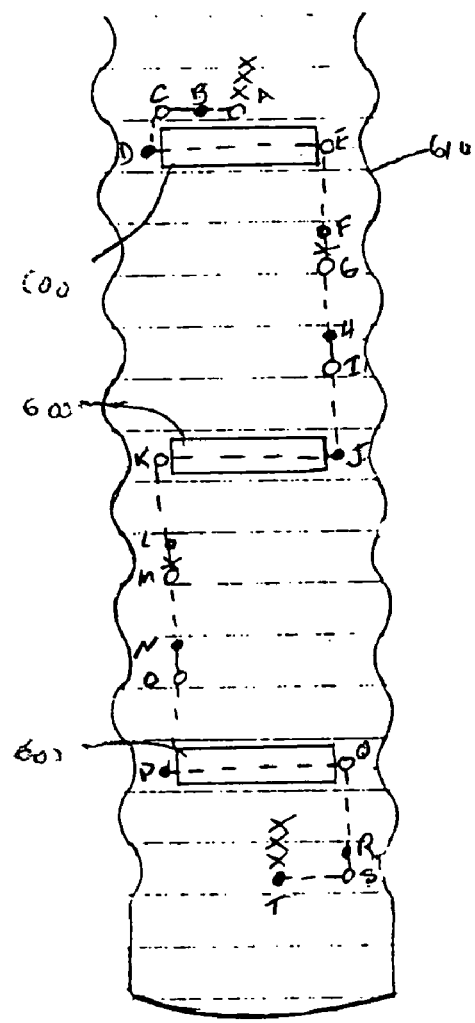
FIG. 28 is a side view, depicting a sixth sewing pattern for attaching devices to a graft.

Other approaches (See FIGS. 21 and 22) for attaching or holding a sensor 310 adjacent a medical device 500 may include providing the medical device 500 with a pocket 510, 512. In a first approach, the pocket 510 can be weaved within the material or otherwise be an integral part of the medical device 500. In a second method, a piece of material 512 can be affixed to the medical device 500 to create a pocket. In both approaches, the pockets 510, 512 are contemplated to be closed about a sensor 310, for example, to thereby provide a secure receptacle for the sensor 310.

In FIGS. 23-28, there are shown various approaches for attaching by sewing radiopaque markers or sensing or other devices 600 to a graft device 610. Each approach involves making stitches entering and exiting the graft 610. As before, the darkened circles represent stitching exiting a graft wall and open circles represent stitching entering a graft wall. The "X's" represent knotting or cross stitching of suture being employed in the sewing process. The dashed lines include suture traversing within an interior of a graft. Moreover, the stitching has been chronologically labeled from A-Z and for the approaches taken in FIGS. 23 and 27 from A-Z and sequentially continuing through A1, B1 etc. Further, although not shown the stitching pattern is repeated in reverse chronological order using a second suture. Knot balls are made in the ends of each suture by making overhand ties and melting the suture. A slightly different approach is taken in FIG. 23 where a single suture is used and there are more stitch points and the single suture crosses the sensing or other devices 610. The approaches shown in FIGS. 24-27 differ in the number of stitch points and knotting or cross stitching but include a common approach in diagonally traversing the sensing device 600. The approach shown in FIGS. 20 is unique in that the sensor or other device 600 is traversed laterally but not diagonally.

While several particular forms of the invention have been illustrated and described, it will be apparent that various modifications can be made without departing from the spirit and scope of the invention. Accordingly, it is not intended that the invention be limited, except as by the appended claims.

What is claimed:

1. A method of protecting a sensor attached to a graft intended to be delivered within vasculature using a catheter, comprising:
    attaching a sensor to a graft;
    attaching a marker to the graft;
    folding portions of the graft to cover the sensor and the marker; and
    placing the graft within a catheter.

2. The method of claim 1, further comprising configuring the graft to define an H-shape.

3. The method of claim 1, further comprising folding more than two layers of graft material over the sensor.

4. The method of claim 1, further comprising placing a double-folded section of graft material over the sensor.

5. The method of claim 1, further comprising placing a single folded section of graft material over the sensor.

6. The method of claim 1, further comprising configuring a membrane of the sensor so that the membrane is substantially perpendicular to a radius of an unfolded graft.

7. The method of claim 1, wherein different portions of the graft are used to cover the sensor and the marker.

8. The method of claim 1, wherein a plurality of markers are attached to the graft.

9. The method of claim 8, wherein the plurality of markers are positioned laterally spaced from the sensor.

10. The method of claim 9, wherein each of the plurality of markers are covered by portions of the graft.

11. The method of claim 1, wherein four layers of the graft are folded over the sensor.

* * * * *